United States Patent [19]

Beguin

[11] 4,174,395
[45] Nov. 13, 1979

[54] 4-[4-(2-METHYL-3-HYDROXY-4-HYDROXYMETHYL-5-PYRIDYL-METHYL)-1-PIPERAZINYL]-6-METHYLPYRIMIDINES

[75] Inventor: Alain Beguin, Meudon, France

[73] Assignee: Societe Civile de Recherches et d'Applications Scientifiques, Paris, France

[21] Appl. No.: 921,335

[22] Filed: Jul. 3, 1978

[30] Foreign Application Priority Data

Jul. 12, 1977 [GB] United Kingdom ............... 29281/77

[51] Int. Cl.$^2$ ................... A61K 31/505; C07D 401/14
[52] U.S. Cl. .................................... 424/251; 544/295; 544/362
[58] Field of Search ......................... 544/295; 424/251

[56] References Cited

U.S. PATENT DOCUMENTS

| | | | |
|---|---|---|---|
| 2,459,367 | 1/1949 | Denton et al. ....................... | 544/295 |
| 2,606,906 | 8/1952 | Hultquist et al. ..................... | 544/295 |
| 2,748,125 | 5/1956 | Hofmann .............................. | 544/295 |

*Primary Examiner*—Paul M. Coughlan, Jr.
*Attorney, Agent, or Firm*—Eyre, Mann, Lucas & Just

[57] ABSTRACT

New derivatives of pyrimidine are disclosed. The disclosed compounds are substituted piperazinyl derivatives of pyrimidine and the pharmaceutically acceptable salts thereof. The compounds show therapeutic value especially in the area of atheromas.

2 Claims, No Drawings

4-[4-(2-METHYL-3-HYDROXY-4-HYDROXYMETHYL-5-PYRIDYL-METHYL)-1-PIPERAZINYL]-6-METHYLPYRIMIDINES

This invention relates to new complex pyrimidine derivatives which are especially interesting for their activity in the field of atheromas, to their preparation and to therapeutic compositions containing the same.

The compounds according to this invention have the general formula:

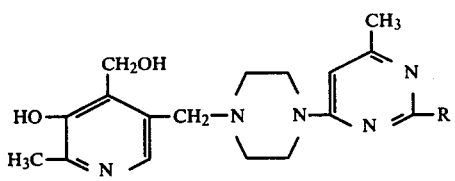

in which R represents a piperidino radical or a 4-(2-methyl-3-hydroxy-4-hydroxymethyl-5-pyridyl-methyl)-1-piperazinyl radical, and therapeutically acceptable salts thereof.

The above compounds can be prepared, by reacting in a polar solvent, at reflux, the piperidine or the 4-(2-methyl-3-hydroxy-4-hydroxymethyl-5-pyridyl-methyl)-1-piperazine on the corresponding chloride:

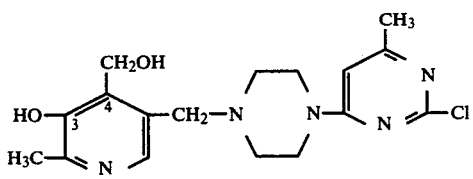

wherein the —OH and —CH$_2$OH groups in 3 and 4 positions of the pyridoxine moiety have been previously blocked, then by heating at about 70°–90° C. the compound thus obtained for breaking the blocking of the said —OH and —CH$_2$OH groups.

The compounds according to this invention together with their therapeutically acceptable salts are especially interesting for their anti-atheromatic activity which, considered in its whole, is generally superior to that of standard reference compounds such as acetyl salicylic acid and its salts, ethyl p-chlorophenoxy-isobutyrate, nicotinic acid and its salts and 2,6-bis(diethanolamine)-4,8-dipiperidinopyrimido-[5,4-d]pyrimidine.

Various experiments have shown a very favourable action of the compounds of the invention on:

(a) the vascular and parietal aspect of the atheromas (test of the oedema by ovalbumin and caragenin on rats; lowering of the capillary permeability on rats);

(b) the platelets aspect (platelets adhesivity in vitro; platelets agglutination in vitro by collagen, adrenalin and adenosine di-phosphate; platelets agglutination in vivo on hamster's cheek pouch); and (c) the fibrolipidic aspect (triton test on rats for triglycerids and cholesterol and experimental hyperlipemia and hypercholesterolemia tests on rabbits).

It has been noticed, for instance, in the case of the last tests on rabbits that the treated animals present a lowering of the total lipids below the figures found for control animals whereas animals having received only the hyperlipidic diet without treatment show a very important increase of lipemia. This does not occur for instance with ethyl p-chlorophenoxy isobutyrate.

In the triton test the protection given by the products of the invention is, for the same doses, 3 times better than the one given by ethyl p-chlorophenoxy-isobutyrate and 2,6-bis (di-ethanolamino), 4,8-dipiperidinopyrimido-[5,4-d]pyrimidine and is comparable to that given by nicotinic acid.

These remarks apply to compounds of both following examples.

Compound of example 2 and its salts seem to be more active and have been found to act very satisfactorily in the same therapeutic field, as exemplified by the following experimentations:

(d) Action on the lipidic parameters of normal rats (method of K. M. Baggaley & al., J. of Medical Chemistry 1977—20 N° 11 p. 1388–1393).

When administered to normal rats, they do not lower the cholesterol and total lipids rates, in contradistinction with 2-methyl-2[4-(4'-chlorobenzoyl) phenoxy] propionic acid, isopropyl ester; this is accordingly a strong advantage.

(e) Action in dyslipemia provoked by fast, on the rabbit. (Method of Ammerman C. B. & al. Am. J. Phys. 1961—200 p. 75–79).

Fast induces, in the rabbit, an increase of triglycerids, cholesterol and β-lipoproteins in the blood. In animals treated with the compound of example 2 or its salts, the rates of these factors remain substantially normal whereas in animals treated with 2-methyl-2[4-(4'-chlorobenzoyl) phenoxy] propionic acid, isopropyl ester, only cholesterol and β-lipoproteins rates remain normal and triglycerids rates are strongly increased (over the rates obtained for rabbits deprived of food and non treated).

TOXICITY

The toxicity of the compounds of examples 1 and 2 has been researched per os on rats and mice: no death for mice at the maximum dose of 4 g/kg and 20% of death for rats at the maximum dose of 3 g/kg. These values confirm the low toxicity of the compounds of the invention.

POSOLOGY—PRESENTATION

For the human therapy, the efficient doses per os are from 1.5 g to 10 g of active compound per diem.

Preferred presentations comprise tablets and gelatine capsules containing 0.25 to 1 g of active compound.

The following Examples illustrate this invention.

EXAMPLE 1

Bis-2,4-[4-(2-methyl-3-hydroxy-4-hydroxymethyl-5-pyridyl-methyl)-1-piperazinyl]-6-methylpyrimidine.

Reaction scheme:

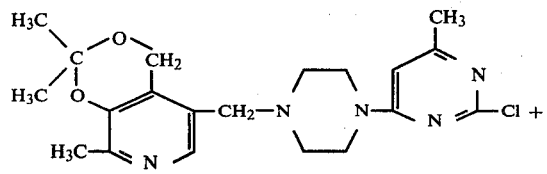

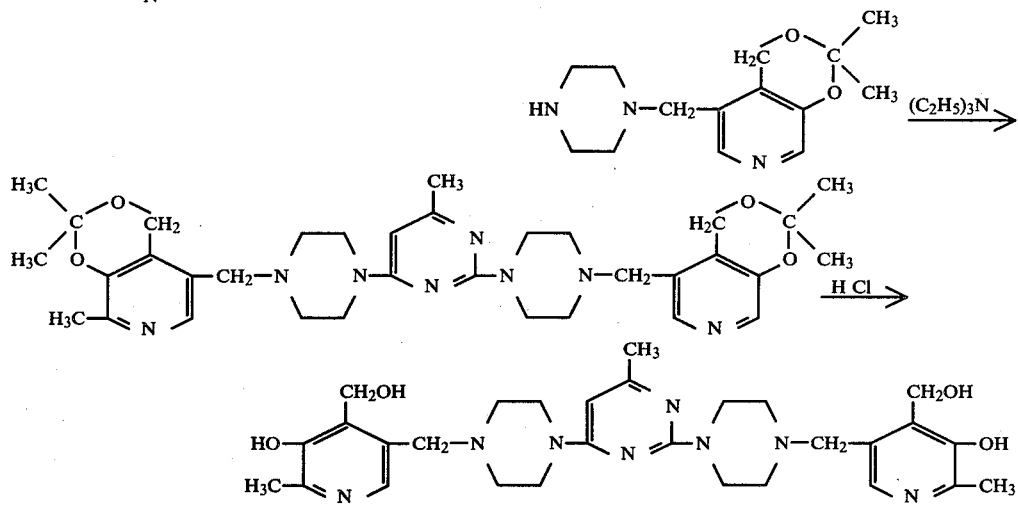

Into a 10-liter reactor fitted with heating, cooling and stirring means, there were placed 277 g (1 mole) of O,O'-isopropylidenyl-2-methyl-3-hydroxy-4-hydroxymethyl-5-(N-piperazinylmethyl)-pyridine, 3 liters of dry acetonitrile, 404 g (1 mole) of 2-chloro-4-[4-(O,O'-isopropylidenyl-2-methyl-3-hydroxy-4-hydroxymethyl-5-pyridyl-methyl)-1-piperazinyl]-6-methylpyrimidine and 102 g (1 mole) of triethylamine. The mixture was stirred and refluxed for 40 hours and then cooled to 5° C.

A precipitate separated was washed with diethyl ether and then with water until free from chloride ions, and was dried to give 515 g (about 80% yield) of bis-2,4-[4-(O,O'-isopropylidenyl-2-methyl-3-hydroxy-4-hydroxymethyl-5-pyridyl-methyl)-1-piperazinyl]-6-methyl-pyrimidine.

The 2-chloro-4-[4-(O,O'-isopropylidenyl-2-methyl-3-hydroxy-4-hydroxymethyl-5-pyridyl-methyl)-1-piperazinyl]-6-methylpyrimidine used as starting material was obtained by reacting O,O'-isopropylidenyl-2-methyl-3-hydroxy-4-hydroxymethyl-5-(N-piperazinylmethyl)-pyridine with 2,4-dichloro-6-methylpyridine in stoichiometric quantities in conditions similar to those described above except that the reflux was continued for only 20 hours.

The 2,4-dichloro-6-methylpyridine was obtained by chlorination of methyluracil using phosphorus oxychloride.

The O,O'-isopropylidenyl-2-methyl-3-hydroxy-4-hydroxymethyl-5-(N-piperazinylmethyl)-pyridine was obtained by blocking the hydroxyl and hydroxymethyl groups at the 3- and 4-positions of pyridoxine by acetone in the presence of hydrochloric acid and reacting the resulting blocked pyridoxine with piperazine.

The bis-2,4-[4-(O,O'-isopropylidenyl-2-methyl-3-hydroxy-4-hydroxymethyl-5-pyridyl-methyl)-1-piperazinyl]-6-methylpyrimidine was treated with hydrochloric acid whilst stirring at about 80° C. for 3 hours. This treatment broke the isopropylidene bridges and there was obtained 435 g (about 77% yield) of the desired product which was a white powder melting at about 240° C. with decomposition. Analysis showed a good correspondence with the formula $C_{29} H_{40} N_8 O_4$.

The compound was found to be insoluble in water, ethanol, chloroform and transcutanol at room temperature but soluble in dimethylsulphoxide in the same conditions.

Dimaleate and monocitrate are readily obtained by the usual routes. These salts are soluble in water.

EXAMPLE 2

2-piperidino-4-[4-(2-methyl-3-hydroxy-4-hydroxymethyl-5-pyridyl-methyl)-1-piperazinyl]-6-methylpyrimidine.

Example 1 was repeated except that the O,O'-isopropylidenyl-2-methyl-3-hydroxy-4-hydroxymethyl-5-(N-piperazinylmethyl)-pyridine was replaced by 1 mole of piperidine. There was obtained the desired product which was a white powder melting at 208° C., in a yield of about 76%. Analysis showed a good correspondence with the formula $C_{22} H_{32} N_6 O_2$. The compound was found to be insoluble at room temperature in water but soluble in chloroform, ethanol, transcutanol and dimethylsulphoxide.

The corresponding monocitrate is a white product melting at 118°–121° C. (Tottoli), fairly soluble in water at room temperature if obtained by crystallization or highly soluble in water, if obtained by lyophilisation.

I claim:

1. New derivatives of pyrimidine of the general formula:

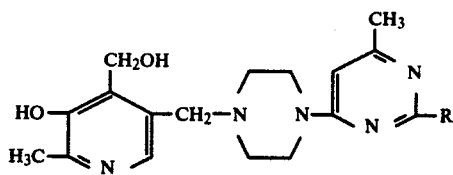

in which R represents a piperidino radical or a 4-(2-methyl-3-hydroxy-4-hydroxymethyl-5-pyridyl-methyl)-1-piperazinyl radical and therapeutically acceptable salts thereof.

2. A composition of matter for therapeutic use comprising as an active ingredient therein one of the compounds according to claim 1, the active ingredient being present in sufficient amount to be effective as an antiatheromal agent, and the active ingredient being incorporated in an appropriate carrier.

* * * * *